United States Patent [19]

Schläepfer

[11] 3,940,417

[45] Feb. 24, 1976

[54] QUATERNISED BENZOFURANYL-BENZIMIDAZOLES

[75] Inventor: Hans Schläepfer, Basel, Switzerland

[73] Assignee: Ciba-Geigy Corporation, Ardsley, N.Y.

[22] Filed: Aug. 22, 1974

[21] Appl. No.: 499,687

Related U.S. Application Data

[63] Continuation of Ser. No. 205,303, Dec. 6, 1971, abandoned.

[30] Foreign Application Priority Data

Dec. 9, 1970 Switzerland................... 18251/70

[52] U.S. Cl................. 260/309.2; 8/1 W; 252/8.8; 252/301.2 W; 252/301.3 W; 260/346.2 R; 260/346.2 M
[51] Int. Cl.².............. C07D 235/12; C07D 307/81
[58] Field of Search................... 260/309.2

[56] References Cited
UNITED STATES PATENTS 3,103,518  9/1963  Duennenberger............. 260/309.2
3,497,525  2/1970  Harnisch et al................. 260/309.2
3,590,047  6/1971  Shen et al....................... 260/309.2
3,637,734  1/1972  Harnisch et al................. 260/309.2
3,772,323  11/1973  Schläpfer et al................ 260/309.2

FOREIGN PATENTS OR APPLICATIONS 1,117,000  11/1961  Germany..................... 260/309.2

OTHER PUBLICATIONS

Schlaepfer Chem. Abstr., 1972, Vol. 77, No. 128095s.

Primary Examiner—Natalie Trousof
Attorney, Agent, or Firm—Joseph G. Kolodny; Edward McC. Roberts; Prabodh I. Almaula

[57] ABSTRACT

The invention relates to new quaternised benzofuranyl-benzimidazole derivatives which can be prepared by known methods. Said compounds are useful as optical brighteners for organic material.

5 Claims, No Drawings

QUATERNISED BENZOFURANYL-BENZIMIDAZOLES

This is a continuation of application Ser. No. 205,303, filed on Dec. 6, 1971, now abandoned.

The present invention relates to new quaternised benzofuranyl-benzimidazole compounds, processes for their manufacture, and their use for the optical brightening of organic materials.

The new compounds correspond to the formula

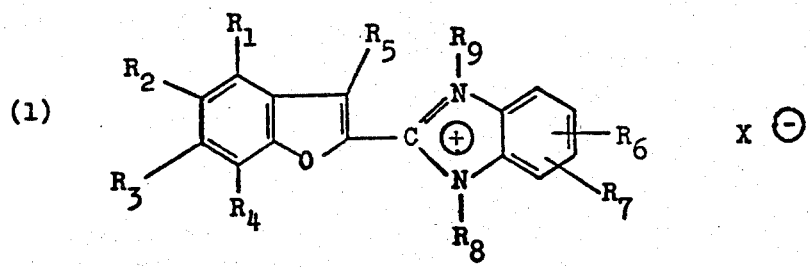

(1)

wherein $R_1$ denotes hydrogen, halogen or a lower alkyl or alkoxy group or together with $R_2$ denotes a fused benzene radical, $R_2$ denotes hydrogen, a lower alkyl or alkoxy group, halogen, a carboxyl, carboalkoxy, aminocarbonyl, monoalkylaminocarbonyl or dialkylaminocarbonyl, sulphonic acid, alkylsulphonyl, alkoxysulphonyl, aminosulphonyl, monoalkylaminosulphonyl or dialkylaminosulphonyl group or together with $R_1$ or $R_3$ denotes a fused benzene radical, $R_3$ denotes hydrogen, halogen or a lower alkyl or alkoxy group or together with $R_2$ or $R_4$ denotes a fused benzene radical, $R_4$ denotes hydrogen, a lower alkyl or alkoxy group or halogen or together with $R_3$ denotes a fused benzene radical, $R_5$ denotes hydrogen, a lower alkyl group or a phenyl group which is optionally substituted by methyl and/or methoxy, $R_6$ denotes hydrogen, a lower alkyl or alkoxy group, halogen, a phenyl radical, an alkylsulphonyl radical or a phenylsulphonyl radical, $R_7$ denotes hydrogen, a lower alkyl or alkoxy group or halogen, $R_8$ denotes a lower alkyl group, a hydroxyalkyl group possessing at least two carbon atoms, the cyanoethyl group, a phenyl radical which is optionally substituted by halogen, lower alkyl or alkoxy groups, a cycloalkyl radical or an aralkyl radical, $R_9$ denotes a lower alkyl group, a hydroxyalkyl group, an alkoxyalkyl group, an optionally substituted aralkyl radical or the $-CH_2CN$, $-CH_2CONH_2$ or $-CH_2-COOR$ radical, wherein R represents an alkyl group with one to four carbon atoms, and X denotes halogen, an alkylsulphonic acid radical or a phenylsulphonic acid radical which is optionally substituted by lower alkyl.

The scope of the formula (1) includes the compounds of the formula

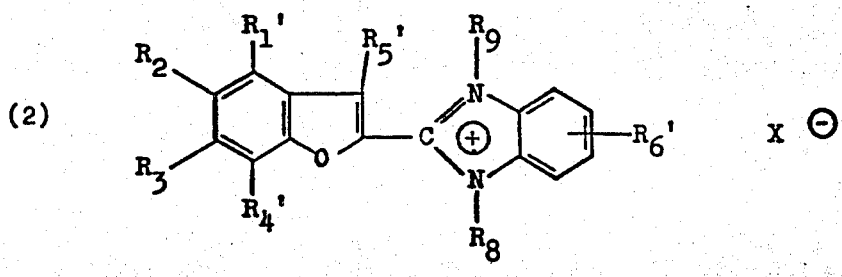

(2)

wherein $R_1'$ denotes hydrogen or a lower alkyl group or together with $R_2$ denotes a fused benzene radical, $R_2$ denotes hydrogen, a lower alkyl or alkoxy group, halogen, a carboxyl, carboalkoxy, aminocarbonyl, monoalkylaminocarbonyl or dialkylaminocarbonyl, sulphonic acid, alkylsulphonyl, alkoxysulphonyl, aminosulphonyl, monoalkylaminosulphonyl or dialkylaminosulphonyl group or together with $R_1'$ or $R_3$ denotes a fused benzene radical, $R_3$ denotes hydrogen or a lower alkyl or alkoxy group or together with $R_2$ or $R_4'$ denotes a fused benzene radical, $R_4'$ denotes hydrogen, a lower alkyl group or halogen or together with $R_3$ denotes a fused benzene radical, $R_5'$ denotes hydrogen, a lower alkyl group or the phenyl group and $R_6'$ denotes hydrogen, a lower alkyl group, an alkoxy group, halogen or a phenyl radical, $R_8$ denotes a lower alkyl group, a hydroxyalkyl group possessing at least two carbon atoms, the cyanoethyl group, a phenyl radical which is optionally substituted by halogen, lower alkyl or alkoxy groups, a cycloalkyl radical or an aralkyl radical, $R_9$ denotes a lower alkyl group, a hydroxyalkyl group, an alkoxyalkyl group, an optionally substituted aralkyl radical or the $-CH_2CN$, $-CH_2CONH_2$ or $-CH_2-COOR$ radical, wherein R represents an alkyl group with one to four carbon atoms, and X denotes halogen, an alkylsulphonic acid radical or a phenylsulphonic acid radical which is optionally substituted by lower alkyl.

Preferred alkyl and alkoxy radicals, where they occur in the compounds of the formulae (1) and (2), are those with one to four carbon atoms, preferably methyl or methoxy. Halogen generally represents bromine and preferably represents chlorine.

Benzofuranes deserving special mention are those of the formula (3) 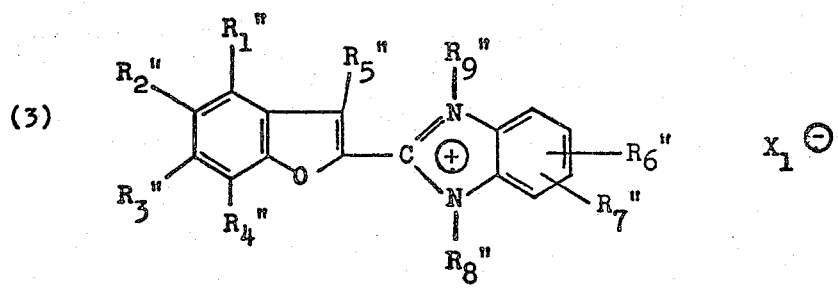 $X_1^{\ominus}$ wherein $R_1''$ denotes hydrogen, methyl, ethyl, methoxy or halogen, preferably chlorine, or together with $R_2''$ denotes a fused benzene radical, $R_2''$ denotes hydrogen, methyl, ethyl, methoxy or halogen, preferably chlorine, or together with $R_1''$ or $R_3''$ denotes a fused benzene radical, $R_3''$ denotes hydrogen, methyl, ethyl, alkoxy with one to four carbon atoms, preferably methoxy, or halogen, preferably chlorine, or together with $R_2''$ or $R_4''$ denotes a fused benzene radical, $R_4''$ denotes hydrogen, alkyl with one to four carbon atoms, preferably methyl, methoxy or halogen, preferably chlorine, or together with $R_3''$ denotes a fused benzene radical, $R_5''$ denotes hydrogen, alkyl with one to four carbon atoms, preferably methyl, or phenyl which is optionally substituted by methyl and/or methoxy, $R_6''$ denotes hydrogen, alkyl with one to four carbon atoms, preferably methyl, alkylsulphonyl with one to four carbon atoms, preferably methylsulphonyl, methoxy or halogen, preferably chlorine, $R_7''$ denotes hydrogen, methyl, methoxy or halogen, preferably chlorine, $R_8''$ denotes alkyl with one to four carbon atoms, preferably methyl, hydroxyalkyl with two to four carbon atoms, cyanoethyl, phenyl which is optionally substituted by chlorine, methyl or methoxy, or cyclohexyl or benzyl, $R_9''$ denotes alkyl with one to four carbon atoms which is optionally substituted by hydroxyl or alkoxy with 1 to 4 carbon atoms, benzyl which is optionally substituted by chlorine or methoxy, or a radical —CH₂CN, —CH₂CONH₂ or —CH₂COOR, wherein R represents an alkyl group with one to four carbon atoms, preferably methyl, and $X_1$ denotes halogen, preferably chlorine, an alkylsulphonic acid radical with 1 to 4 carbon atoms, preferably the methylsulphonic acid radical, or a phenylsulphonic acid radical which is optionally substituted by methyl.

Further types of compounds to be highlighted are those of the formula (4) 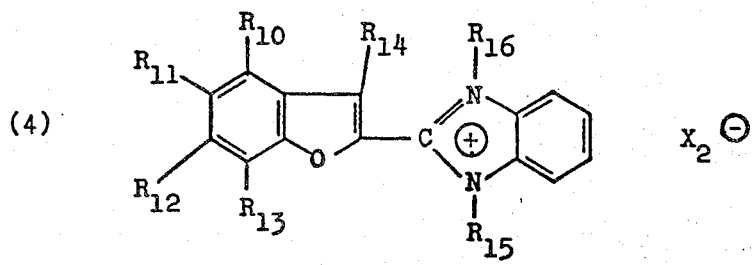 $X_2^{\ominus}$ wherein $R_{10}$ denotes hydrogen or together with $R_{11}$ denotes a fused benzene radical, $R_{11}$ denotes hydrogen or halogen or together with $R_{10}$ denotes a fused benzene radical, $R_{12}$ denotes hydrogen or an alkyl or alkoxy group with one to four carbon atoms each, $R_{13}$ denotes hydrogen or halogen, $R_{14}$ denotes hydrogen or an alkyl group with one to four carbon atoms, $R_{15}$ denotes an alkyl group with one to four carbon atoms, $R_{16}$ denotes an alkyl or hydroxyalkyl group with one to four carbon atoms or an aralkyl group and $X_2$ denotes halogen, an alkylsulphonic acid radical or the methylphenylsulphonic acid radical.

Of outstanding interest here are the benzofuranes of the formula (5) 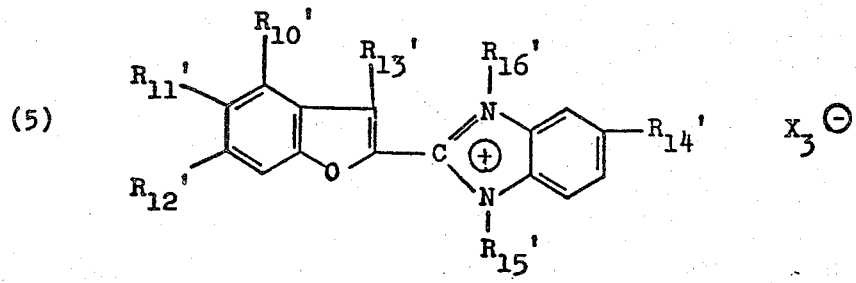 $X_3^{\ominus}$ wherein $R_{10}'$ and $R_{11}'$ denote hydrogen or together denote a fused benzene radical, $R_{12}'$ denotes hydrogen, methoxy or methyl $R_{13}'$ denotes hydrogen or methyl, $R_{14}'$ denotes hydrogen, methyl, methoxy, chlorine or methylsulphonyl, $R_{15}'$ denotes methyl, phenyl or benzyl, $R_{16}'$ denotes methyl or benzyl and $X_3$ denotes chlorine, the methylsulphonic acid radical or the p-toluenesulphonic acid radical.

Amongst the compounds of the formulae (1) to (5), those in which not more than three of the R-substituents located on carbon atoms have a meaning other than hydrogen are generally preferred.

Compounds of the formula (6) 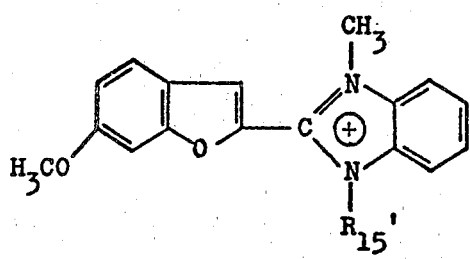

wherein $R_{15}'$ denotes methyl, phenyl or benzyl and $X_4$ denotes halogen, the methylsulphonic acid radical or the methylphenylsulphonic acid radical are of particular practical interest.

The new compounds are used for imparting a white shade to organic material, for example natural fibre material such as, say, cotton, above all synthetic fibres, for example of polyesters such as poly(terephthalic acid glycol esters), polyamides such as polymers based on hexamethylenediamine adipate or caprolactam, cellulose esters, such as cellulose 2½-acetate and cellulose triacetate, and especially polyacrylonitrile.

The organic material can, for example, be brightened by incorporating therein small amounts of optical brighteners according to the invention, appropriately 0.001 to 1% relative to the material to be brightened, optionally together with other substances, such as plasticisers, stabilisers or pigments. The brighteners can, for example, be incorporated into the plastics as solutions in plasticisers, such as dioctyl phthalate, or together with stabilisers, such as dibutyl-tin dilaurate or sodium pentaoctyl-tripolyphosphate, or together with pigments, for example titanium dioxide. Depending on the nature of the material to be brightened, the brightener can also be dissolved in the monomers before polymerisation, in the polymer composition or, together with the polymers, in a solvent. The material pretreated in this way is thereafter converted into the desired final form in accordance with processes which are in themselves known, such as spinning and stretching. The brighteners can also be incorporated into finishes, for example into finishes for textile fibres such as polyvinyl alcohol, or into resins or resin precondensates, such as, for example, methylol compounds of ethyleneurea, which serve for the treatment of textiles.

The compounds according to the invention are also suitable for brightening paper by surface coating.

Preferably, however, colourless high molecular organic material in the form of fibres is brightened. To brighten these fibre materials, an aqueous solution or dispersion of benzofuranes according to the invention, of the formula (1), is advantageously used. The brightener dispersion or solution in that case preferably contains from 0.005 to 0.5% of benzofurane according to the invention, relative to the fibre material. Additionally, the dispersion can contain auxiliaries, such as dispersing agents, for example condensation products of fatty alcohols containing 10 to 18 carbon atoms, or of alkylphenols, with 15 to 25 mols of ethylene oxide, or condensation products of alkylmonoamines or polyamines possessing 16 to 18 carbon atoms with at least 10 mols of ethylene oxide, organic acids such as formic acid, oxalic acid or acetic acid, detergents, swelling agents such as dichlorobenzenes or trichlorobenzenes, wetting agent such as sulphosuccinic acid alkyl esters, bleaching agents such as sodium chlorite, peroxides or hydrosulphites, and, if appropriate, brighteners of other categories, such as, for example, stilbene derivatives which possess an affinity for cellulose.

The brightening of the fibre material with the aqueous brightener liquor either takes place by the exhaustion process, at temperatures of, preferably, 30° to 150°C, or by the padding process. In the latter case, the goods are impregnated with a brightener dispersion of, for example, 0.2 to 0.5% strength, and the goods to be dried are finished, for example, by dry or moist heat treatment, for example by steaming at 2 atmospheres or by drying followed by brief dry heating to 180° to 220°C, the fabric being heat-set at the same time, if appropriate. The fibre material treated in this way is finally rinsed and dried.

Colourless, high molecular, organic material optically brightened according to the invention, especially natural or synthetic fibre material brightened in accordance with the exhaustion process, shows a pleasing, pure white appearance with a blue-violet to bluish-tinged fluorescence whilst such fibre material which has been dyed in light colour shades and been whitened according to the invention is distinguished by a pure colour shade.

Wash liquors which contain benzofuranes of the formula (1), when used for washing, impart a brilliant appearance in daylight to the textile fibres treated therewith, for example synthetic polyamide, polyester and cellulose ester fibres, but especially polyacrylonitrile fibres.

The manufacture of compounds of the formula (1) starts from the corresponding non-quaternised compounds of the formula (7) 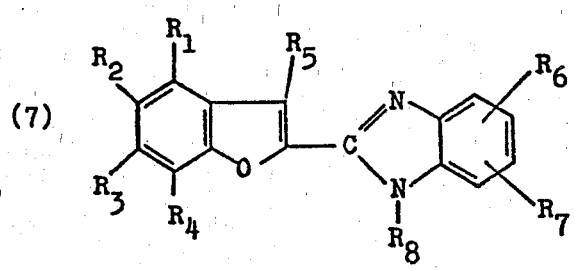

wherein $R_1$ to $R_8$ have the abovementioned meaning, which can be manufactured in accordance with known methods from known starting substances.

The manufacture of the benzimidazoles of the formula (7), wherein $R_8$ denotes an alkyl, cycloalkyl or aralkyl group, for example starts from the corresponding N-substituted o-nitroaniline, which is acylated with optionally substituted coumarilic acid (coumarone-2-carboxylic acid) or a functional derivative thereof, after which either the nitro group is reduced in an acid medium, with simultaneous cyclisation to give the benzimidazole, for example by means of stannous chloride/hydrochloric acid, or the nitro group is reduced under conditions which do not cause cyclisation of the o-amino-acylamino compound to give the benzimidazole (Béchamp reduction) and cyclisation is subsequently brought about by acid condensation agents, such as hydrochloric acid. Analogously substituted compounds can be manufactured from benzimidazoles of the formula (7), in which $R_8$ represents hydrogen, if such N-unsubstituted benzimidazoles are reacted with alkylating or aralkylating agents in the presence of basic compounds, in accordance with known processes.

Benzimidazoles of the formula (7), wherein $R_8$ denotes an alkyl, cycloalkyl or aralkyl group, but especially an aryl group, can be manufactured from N-monosubstituted o-phenylenediamines or optionally substituted 2-aminodiphenylamine, if these are acylated with optionally substituted coumarilic acid or a functional derivative thereof and the corresponding substituted primary acyl-o-phenylenediamine is cyclised in the presence of acid condensation agents, such as hydrochloric acid.

As examples of coumarilic acids there may be mentioned: 3-methylcoumarilic acid, 4-methylcoumarilic acid, 5-methylcoumarilic acid, 6-methylcoumarilic acid, 7-methylcoumarilic acid, 5-ethyl-coumarilic acid, 6-ethylcoumarilic acid, 3-(2-methoxyphenyl)-coumarilic acid, 3,4-dimethyl-coumarilic acid, 3,5-dimethylcoumarilic acid, 3,6-dimethyl-coumarilic acid, 3,7-dimethylcoumarilic acid, 4,6-dimethylcoumarilic acid, 5,6-dimethylcoumarilic acid, 5,7-dimethylcoumarilic acid, 6,7-dimethylcoumarilic acid, 3-phenyl-6-methyl-coumarilic acid, 3-phenyl-5-methyl-coumarilic acid, 3-(2-methoxy-5-methylphenyl)-5-methyl-coumarilic acid, 3-isopropyl-6-methyl-coumarilic acid, 3,4,6-trimethylcoumarilic acid, 4,6-dimethyl-3-isopropylcoumarilic acid, 3,5,6-trimethylcoumarilic acid, 3,4-dimethyl-7-isopropylcoumarilic acid, 4,6-dimethyl-3-ethylcoumarilic acid, 5-chlorocoumarilic acid, 5-bromocoumarilic acid, 6-chlorocoumarilic acid, 7-chlorocoumarilic acid, 3-methyl-5-chlorocoumarillic acid, 3-methyl-5-bromocoumarilic acid, 6-chloro-7-methylcoumarilic acid, 3,6-dimethyl-5-chlorocoumarilic acid, 3,6-dimethyl-5-bromocoumarilic acid, 3-ethyl-5-chloro-6-methylcoumarilic acid, 5,7-dichlorocoumarilic acid, 5,7-dibromocoumarilic acid, 5,7-dibromo-6-methyl-coumarilic acid, 3-methyl-5,7-dibromocoumarilic acid, 4-methoxycoumarilic acid, 5-methoxycoumarilic acid, 6-methoxycoumarilic acid, 7-methoxycoumarilic acid, 3-methyl-4-methoxycoumarilic acid, 3-methyl-5-methoxycoumarilic acid, 3-methyl-6-methoxycoumarilic acid, 3-methyl-7-methoxycoumarilic acid, 3-methyl-6-butyoxycoumarilic acid, 3-methyl-5-ethyl-6-methoxycoumarilic acid, 3,7-dimethyl-6-methoxycoumarilic acid, 3-methyl-5-methoxy-6-bromocoumarilic acid, 3-methyl-5-bromo-6-methoxycoumarilic acid, 3-methyl-4-bromo-5-methoxycoumarilic acid, 3-methyl-4-methoxy-7-bromocoumarilic acid, 5-chloro-6-methoxycoumarilic acid, 5-bromo-6-methoxycoumarilic acid, 4-ethyl-7-methoxycoumarilic acid, 5-ethyl-7-methoxycoumarilic acid, 4-ethyl-5-methoxycoumarilic acid, 3-methyl-4-methoxy-5,7-dibromocoumarilic acid, 3,6-dimethyl-4-methoxy-5,7-dibromocoumarilic acid, 4,6-dimethoxycoumarilic acid, 6,7-dimethoxycoumarilic acid, 5,6-dimethoxycoumarilic acid, 3-methyl-4,6-dimethoxycoumarilic acid, 3-methyl-6,7-dimethoxycoumarilic acid, 3-methyl-5,6-dimethoxycoumarilic acid, 4,6-dimethoxy-7-methylcoumarilic acid, 4,6-dimethoxy-5-methylcoumarilic acid, 3-phenyl-5,6-dimethoxycoumarilic acid, 3-phenyl-4,6-dimethoxycoumarilic acid, 3-phenyl-6,7-dimethoxycoumarilic acid, 5,6-dimethoxy-3-methyl-7-bromocoumarilic acid, 3-methyl-4-bromo-5,6-dimethoxycoumarilic acid, 3,5-dimethyl-4,6-dimethoxycoumarilic acid, 3,7-dimethyl-4,6-dimethoxycoumarilic acid, 3-methyl-7-chloro-4,6-dimethoxycoumarilic acid, 3-methyl-7-bromo-4,6-dimethoxycoumarilic acid, 4-methyl-5-bromo-6-methoxycoumarilic acid, 3-methyl-6-methoxy-7-bromocoumarilic acid, 3-phenyl-6-methoxycoumarilic acid, 3-(m-methoxyphenyl)-6-methoxycoumarilic acid, 3-(p-methoxyphenyl)-6-methoxycoumarilic acid, 3-methyl-6-methoxy-5,7-dibromocoumarilic acid, 5-methoxy-7-chlorocoumarilic acid, 5-methoxy-7-bromocoumarilic acid, 4,5,6-trimethoxycoumarilic acid, 4,6,7-trimethoxycoumarilic acid, 3-phenyl-4,5,6-trimethoxycoumarilic acid, 3-phenyl-5,6,7-trimethoxycoumarilic acid, 4,6,7-trimethoxy-5-methylcoumarilic acid, 4,6,7-trimethoxy-5-bromocoumarilic acid, 3-methyl-6,7-benzocoumarone-2-carboxylic acid, 3-ethyl-6,7-benzocoumarone-2-carboxylic acid, 3-isopropyl-6,7-benzocoumarone-2-carboxylic acid, 5-methoxy-6,7-benzocoumarone-2-carboxylic acid, 3-methyl-5-methoxy-6,7-benzocoumarone-2-carboxylic acid, 3-methyl-4,5-benzocoumarone-2-carboxylic acid and 5,6-benzocoumarone-2-carboxylic acid.

As examples of substituted o-nitroanilines there may be mentioned: 2-nitro-4-chloroaniline, 2-nitro-4-methoxyaniline, 2-nitro-4-methylaniline, 2-nitro-4-methylsulphonylaniline, 2-nitro-4-chloro-5-methylaniline, 2-nitro-3-methyl-5-bromoaniline, 2-nitro-4-tert-butylaniline, 2-nitro-4-methoxy-5-methylaniline, 2-nitro-4-ethylsulphonylaniline, 2-nitro-3-chloro-5-methoxyaniline, 2-nitro-5,6-dimethylaniline, 2-nitro-4,6-dichloroaniline, o-nitro-N-methylaminobenzene, o-nitro-(β-cyanoethylamino)-benzene, o-nitro-(β-hydroxyethylamino)-benzene, o-nitro-N-ethylaminobenzene, o-nitro-N-butylaminobenzene, o-nitro-N-cyclohexylaminobenzene, o-nitro-N-benzylaminobenzene and 2-nitro-4-methyl-N-methylaminobenzene.

As examples of o-phenylenediamines there may be mentioned: 2-amino-diphenylamine, 3-chloro-2-amino-diphenylamine, 4-chloro-2-amino-diphenylamine, 5-chloro-2-amino-diphenylamine, 5-fluoro-2-amino-diphenylamine, 3'-chloro-2-amino-diphenylamine, 4'-chloro-2-amino-diphenylamine, 4'-bromo-2-aminodiphenylamine, 4,3'-dichloro-2-aminodiphenylamine, 4,4'-dichloro-2-amino-diphenylamine, 4,5'-dichloro-2-amino-diphenylamine, 4-methyl-2-amino-diphenylamine, 5-chloro-3'-methyl-2-amino-diphenylamine, 4-methoxy-2-amino-diphenylamine and 4'-methoxy-2-amino-diphenylamine.

The quaternisation reaction then takes place in accordance with the equation:

(7) 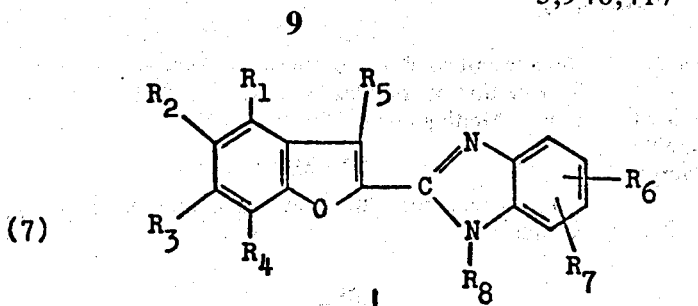

+ R₉X (1) 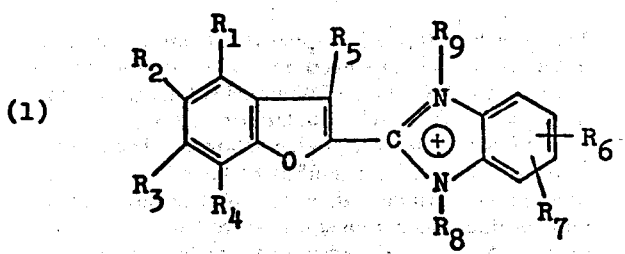  X⁻

This quaternisation is carried out in a solvent which is inert towards the reactants, at temperatures of 0° to 200°C, preferably at 20° to 150°C. Such solvents are, for example, aromatic hydrocarbons such as benzene, toluene and xylene; halogenated hydrocarbons such as methylene chloride, tetrachloroethylene, chlorobenzene, bromobenzene or dichlorobenzene, and also nitrobenzene, lower alkanols and open or cyclic ethers, such as ethanol, isopropanol, butanol, diethyl ether, dibutyl ether, ethylene glycol monomethyl ether, ethylene glycol monoethyl ether, tetrahydrofurane or dioxane; lower ketones such as acetone or methyl ethyl ketone; fatty acid amides such as dimethylformamide or dimethylacetamide; sulphoxides such as dimethylsulphoxide and ureas such as tetramethylurea. If desired, the quaternary salts produced can be converted into other salts by double decomposition.

The reaction described above can in principle be carried out with any quaternising agent. Examples of such quaternising agents are alkyl halides, such as methyl iodide, butyl bromide, dialkyl sulphates such as dimethyl sulphate or diethyl sulphate, aralkyl halides such as benzyl chloride or bromide, halogenoacetic acid esters and their derivatives, and esters of benzenesulphonic acid or of p-toluenesulphonic acid, especially their methyl or ethyl esters.

The new quaternary compounds form yellowish water-soluble powders, the dilute aqueous solutions of which show a vivid blue fluorescence in daylight.

EXAMPLE 1

To manufacture the quaternary compound of the formula (8) 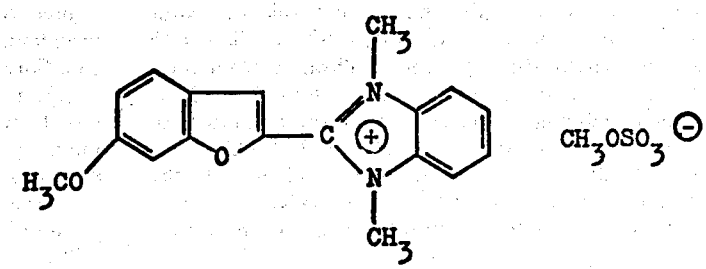

18.1 g of 6-methoxy-2-[1-methyl-benzimidazolyl-(2)]-benzofurane are dissolved in 270 ml of dioxane at 45°C. 10.0 g of dimethyl sulphate are added to the solution, whilst stirring, whereupon the quaternary ammonium salt precipitates after a short time. The reaction mixture is stirred for a further 2 hours at 72° to 75°C and is then cooled to 15°C, and the product is filtered off, rinsed with twice 25 ml of dioxane and dried in vacuo at 60°C. Crude yield: 25 g, corresponding to 97.5% of theory. After one recrystallisation from isopropanol, the almost colourless compound melts at 224° to 225.5°C.

The compound dissolves in water to give a blue-violet fluorescence in daylight and is outstandingly suitable for brightening organic materials, especially polyacrylonitrile fibres.

The 6-methoxy-2-[1-methyl-benzimidazolyl-(2)]-benzofurane used as the starting product is manufactured as follows:

10.5 g of 6-methoxy-coumarilic acid chloride are introduced, over the course of 10 minutes, into a solution of 7.6 g of N-methyl-o-nitroaniline in 85 ml of pyridine at room temperature. The reaction mixture is stirred for 3 hours at room temperature and is then warmed for 1 hour to 80° – 85°C and thereafter poured into water, whereupon the acylation product first separates out as an oil, which crystallises after a short time. After drying and one recrystallisation from benzene-petroleum ether, 6-methoxy-coumarilic acid N-methyl-o-nitroanilide is obtained in almost colourless cubic crystals which melt at 105.5° to 106.5°C.

13.0 g of the acylation product described above are stirred with 400 ml of ethylene glycol monomethyl ether and 42.0 g of stannous chloride.2H$_2$O, dissolved in 84 ml of 37.3% strength hydrochloric acid, are added over the course of 15 minutes at 80° to 90°C. The reaction mixture is subsequently stirred for 3 hours at 104° to 106°C and after cooling is poured into 1,800 ml of 10% strength sodium hydroxide solution, and the ethylene glycol monomethyl ether is azeotropically distilled from the resulting solutions together with water, under reduced pressure, whereupon the compound separates out towards the end of the distillation. After cooling, the product is separated off, washed with water and dried. Repeated recrystallisation from chloroform-petroleum ether (1:2) yields 6-methoxy-2-[1-methyl-benzimidazolyl-(2)]-benzofurane in almost colourless crystals which melt at 151° to 151.5°C.

If, instead of 6-methoxy-coumarilic acid chloride, the equivalent amount of 3-methyl-6-methoxy-coumarilic acid chloride is used and in other respects the procedure described above is followed, 3-methyl-6-methoxy-2-[1-methyl-benzimidazolyl-(2)]-benzofurane is obtained. Melting point: 159° to 159.5°C.

EXAMPLE 2

To manufacture the quaternary compound of the formula

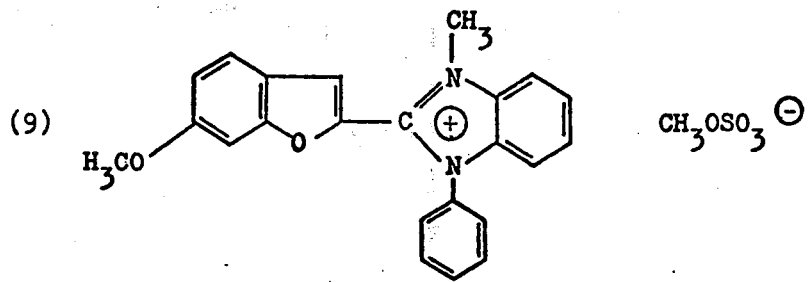

(9)

11.9 g of 6-methoxy-2-[1-phenyl-benzimidazolyl-(2)]-benzofurane are dissolved in 90 ml of dioxane by warming to 85°C. 9.0 g of dimethyl sulphate are added with good stirring. The quaternary salt separates out after a few minutes as a golden yellow oil. The reaction mixture is stirred for 1 hour at 85°C and the solvent is subsequently distilled off in vacuo. The oily evaporation residue which remains is stirred with 750 ml of water at 50° to 55°C and in order to hydrolyse excess dimethyl sulphate, 10% strength sodium carbonate solution is slowly added until a weakly alkaline reaction persists (pH value about 7.5 to 8.0). A little unchanged starting product is then filtered off, the filtrate is clarified with active charcoal and the aqueous solution is evaporated to dryness in vacuo. The evaporation residue is warmed to the boil with 300 ml of methyl ethyl ketone, insoluble inorganic salts are filtered off and thereafter the filtrate is concentrated to a volume of 180 to 200 ml. After 24 hours the crystals which have separated out are separated off and again recrystallised from methyl ethyl ketone. The quaternary salt is obtained as almost colourless fine crystals, joined together in bundles, of melting point 158.5° to 160°C. Yield: 6.25 g.

The quaternary compound dissolves in water to give a blue fluorescence in daylight and is suitable for brightening organic materials, especially polyacrylonitrile fibres.

If, instead of 6-methoxy-2-[1-phenyl-benzimidazolyl-(2)]-benzofurane, the equivalent amount of 6-methoxy-2-[1-benzyl-benzimidazolyl-(2)]-benzofurane is used, and in other respects the procedure described in the example is followed, the quaternary compound of the formula (10)

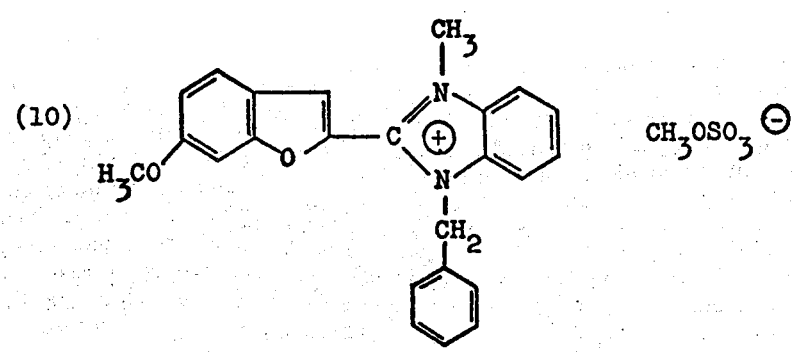

is obtained; after twice crystallising from isopropanol, this compound is in the form of almost colourless crystals which melt at 155° to 155.5°C. This product possesses similar properties to the compound described above.

If instead of 6-methoxy-2-[1-phenyl-benzimidazolyl-(2)]-benzofurane the equivalent amount of 6-methoxy-2-[1-cyclohexyl-benzimidazolyl-(2)]-benzofurane is used and in other respects the procedure described in the example is followed, the quaternary compound of the formula

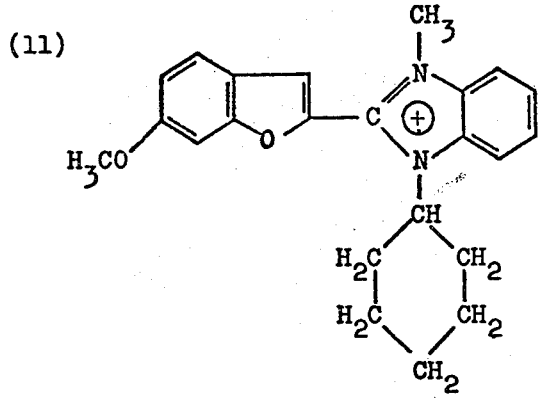

(11)

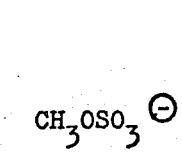

is obtained.

The 6-methoxy-2-[1-phenyl-benzimidazolyl-(2)]-benzofurane used as the starting product is manufactured as follows:

21.7 g of 6-methoxycoumarilic acid chloride are rapidly introduced into a solution of 18.4 g of 2-amino-diphenylamine in 200 ml of pyridine at room temperature, whilst stirring. In the course thereof, the temperature of the reaction mixture rises to about 45°C. After 15 minutes, the reaction mixture is additionally warmed to 80° – 85°C for 1 hour to complete the reaction, and the dark solution is then poured into a copious amount of water. The acylation product, which is brownish-pink in colour and first separates out in a smeary form solidifies after several hours and is then filtered off, washed with water and dried. After recrystallisation from ethanol, 31.5 g (88% of theory) of 2-[6-methoxycoumaroylamido]-diphenylamine are obtained. Melting point 141° to 142°C.

17.9 g of 2-[6-methoxycoumaroylamido]-diphenylamine are stirred with 180 ml of ethylene glycol monomethyl ether and 15.0 g of 37.3% strength hydrochloric acid are added; the reaction mixture is warmed to 100° – 105°C and is kept for 4 hours at this temperature under slight reflux. Thereafter, the strongly fluorescent reaction solution is poured into a mixture of 18 ml of 30% strength sodium hydroxide solution and 1,800 ml of water, whereupon the reaction product first separates out in a somewhat smeary form. After standing for several hours, the product which has solidified is separated off, comminuted, washed with water until free of alkali and dried. 14.6 g (85.8% of theory) of crystals of a dark brownish red colour, of melting point 151° to 155°C, are obtained. Recrystallisation from toluene and treatment with decolourising charcoal and fuller's earth yields the compound of the above formula as almost colourless crystals of melting point 161° to 162°C.

If, instead of 2-amino-diphenylamine, the equivalent amount of N-cyclohexyl-1,2-phenylenediamine or N-benzyl-1,2-phenylenediamine is used, and in other respects the procedure described above is followed, 6-methoxy-2-[1-cyclohexyl-benzyimidazolyl-(2)]-benzofurane or 6-methoxy-2-[1-benzyl-benzimidazolyl-(2)]-benzofurane, respectively, are obtained.

If instead of 2-amino-diphenylamine the equivalent amount of N-benzyl-1,2-phenylenediamine is used and instead of 6-methoxy-coumarilic acid chloride the equivalent amount of 6-methylcoumarilic acid chloride or 5,7-dichlorocoumarilic acid chloride is used, and in other respects the procedure described above is followed, 6-methyl-2-[1-benzyl-benzimidazolyl-(2)]-benzofurane of melting point 172° to 173°C or 5,7-dichloro-2-[1-benzyl-benzimidazolyl-(2)]-benzofurane of melting point 177° to 178°C are respectively obtained.

EXAMPLE 3

To manufacture the quaternary compound of the formula

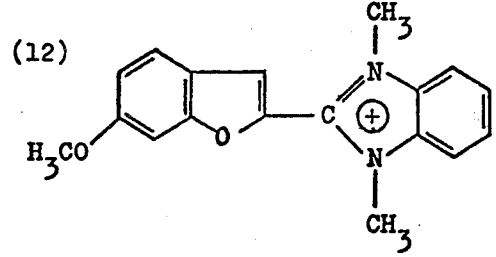

(12)

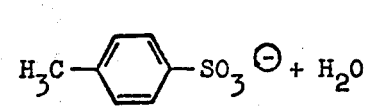

12.5 g of 6-methoxy-2-[1-methyl-benzimidazolyl-(2)]-benzofurane are dissolved in 150 ml of toluene by warming to about 65°C. 12.5 g of p-toluenesulphonic acid methyl ester are then added whilst stirring. The quaternary salt rapidly precipitates as crystals. The reaction mixture is stirred for a further 2 hours at 100°C and after cooling the product is filtered off, washed with toluene and dried. Yield 18.85 g, corresponding to 90% of theory. After one recrystallisation from water with the addition of active charcoal, the salt forms almost colourless crystals which contain 1 mol of water of crystallisation and melt at 204° to 205°C.

The compound dissolves in water to give a blue-violet fluorescence in daylight.

(15)

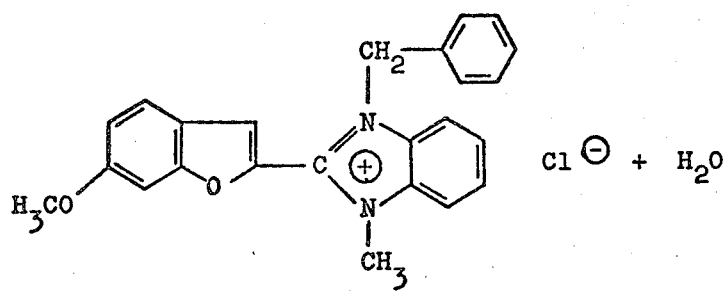

The compound is outstandingly suitable for brightening organic materials, especially polyacrylonitrile fibres.

EXAMPLE 4

To manufacture the quaternary compound of the formula (13)

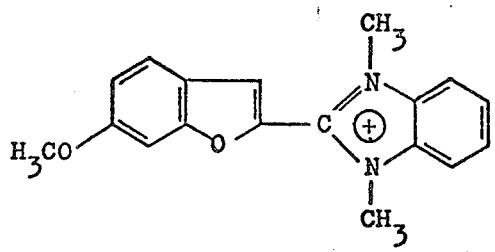

14.0 g of 6-methoxy-2-[1-methyl-benzimidazolyl-(2)]-benzofurane, 150 ml of 95% strength alcohol and 7.5 g of methyl chloride are heated to 100° - 105°C in a pressure vessel for 2½ hours. After cooling and releasing the pressure, the reaction mixture is evaporated to dryness and the evaporation residue is twice recrystallised from water with the addition of active charcoal. The quaternary compound is obtained as pale yellow-greenish tinged fine small needles containing 3 mols of water of crystallisation and melting at 212° to 213°C.

The compound dissolves in water to give a blue-violet fluorescence in daylight and is outstandingly suitable for brightening organic materials, especially polyacrylonitrile fibres.

If instead of 6-methoxy-2-[1-methyl-benzimidazolyl-(2)]-benzofurane the equivalent amount of 3-methyl-6-methoxy-2-[1-methyl-benzimidazolyl(2)]-benzofurane is used and in other respects the procedure described in the example is followed, the quaternary compound of the formula (14)

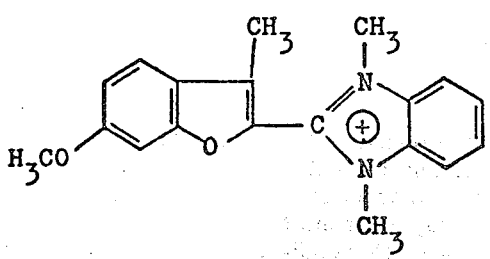

is obtained, which after one recrystallisation from water is in the form of colourless crystals with a mother-of-pearl glitter, which melt with decomposition at 229° to 231°C. This product possesses similar properties to the compound described above.

EXAMPLE 5

To manufacture the quaternary compound of the formula 10 g of 6-methoxy-2-[1-methyl-benzimidazolyl(2)]-benzofurane are heated with 40 g of benzyl chloride for 1 hour to 130°–135°C whilst stirring, whereupon the quaternary salt precipitates after some time, in the form of crystals. After cooling, the precipitate is filtered off, washed with ethyl acetate, dried and recrystallised from water. 7.5 g of pale yellow crystal flakes are obtained, which contain 1 mol of water of crystallisation and melt at 206.5° to 207°C.

The compound dissolves in water to give a blue-violet fluorescence and is suitable for brightening organic materials, especially polyacrylonitrile fibres.

If instead of 6-methoxy-2-[1-methyl-benzimidazolyl-(2)]-benzofurane an equivalent amount of 3-methyl-6-methoxy-2-[1-methyl-benzimidazolyl-(2)]-benzofurane or 6-ethoxy-2-[1-methyl-benzimidazolyl-(2)]-benzofurane or 6-methoxy-2-[1-methyl-5-methyl-benzimidazolyl-(2)]-benzofurane is used, and in other respects the procedure described in the example is followed, the quaternary compound of the formula

(16) 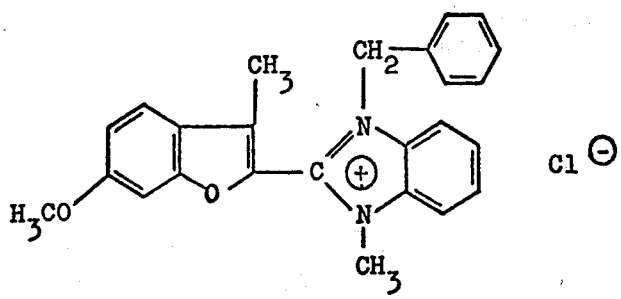

or

(17) 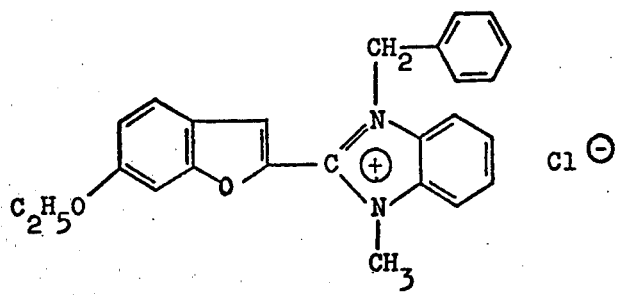

or

(18) 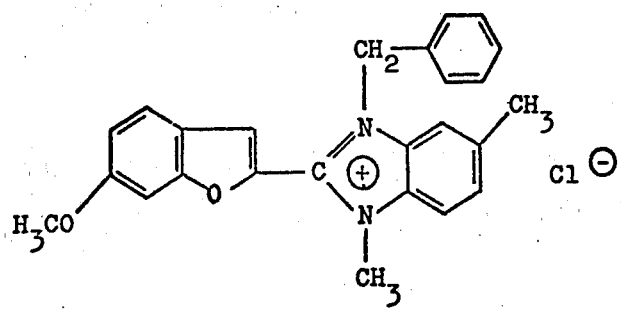

is respectively obtained. These products possess similar properties to the compound manufactured above and are therefore suitable for brightening organic materials, especially polyacrylonitrile fibres.

EXAMPLE 6

To manufacture the quaternary compound of the formula

(19) 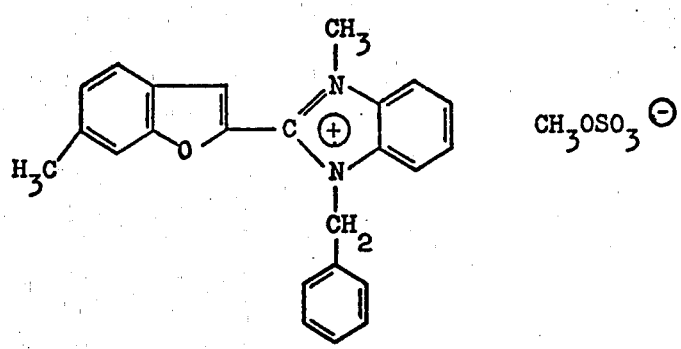

6.72 g of 6-methyl-2-[1-benzyl-benzimidazolyl-(2)]-benzofurane are dissolved in 67 ml of dioxane at 80° to 90°C and 3.15 g of dimethyl sulphate are added dropwise, whilst stirring, whereupon the quaternary salt precipitates after a short time. After stirring for a further hour at 80° to 85°C, the mixture is allowed to cool to room temperature and the product is filtered off, washed with dioxane and dried in vacuo at 60°C. After twice recrystallising from water, 6.25 g of colourless crystal flakes are obtained, which melt at 189.5° to 190.5°C.

The quaternary compound is suitable for brightening organic materials, especially polyacrylonitrile fibres.

If instead of 6-methyl-2-[1-benzyl-benzimidazolyl-(2)]-benzofurane an equivalent amount of 6-methoxy-2-[1-benzyl-5-methyl-benzimidazolyl-(2)]-benzofurane or 6-methoxy-2-[1-benzyl-5-chloro-benzimidazolyl-(2)]-benzofurane or 6-methoxy-2-[1-benzyl-5-methylsulphonyl-benzimidazolyl-(2)]-benzofurane or 3-methyl-6-methoxy-2-[1-methyl-benzimidazolyl-(2)]-benzofurane or 5,7-dichloro-2-[1-benzyl-benzimidazolyl-(2)]-benzofurane is used and in other respects the procedure described in the example is followed, the quaternary compounds of the formulae
(20)
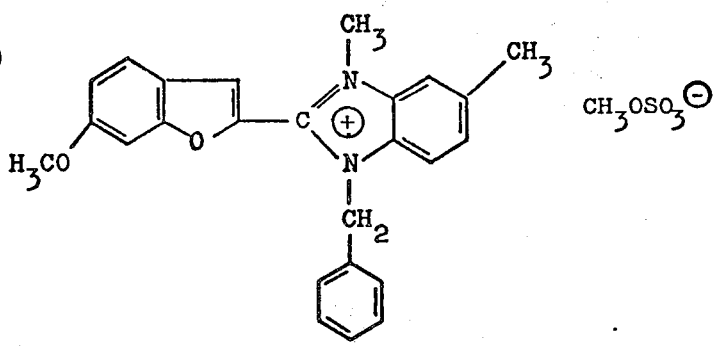
Melting point: 144°–146°C
(21)
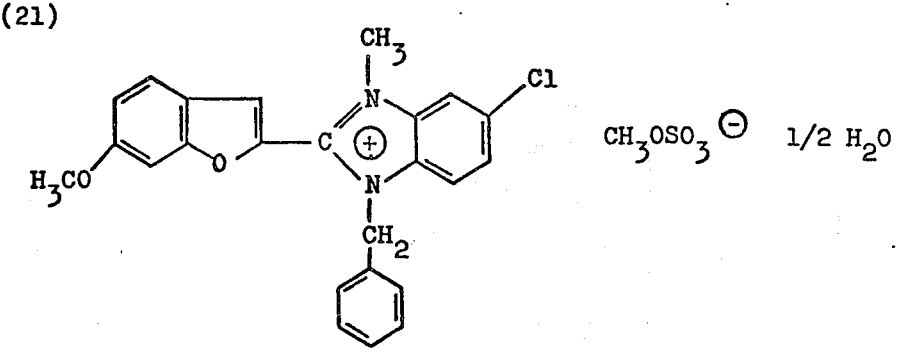
Melting point: 178°–181°C
(22)
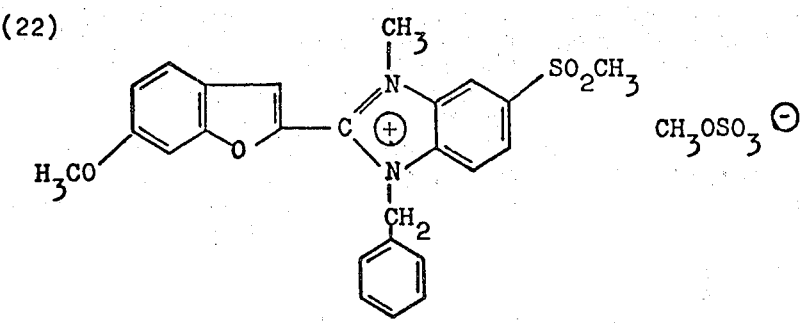
Melting point: 199°–200°C.
(23)
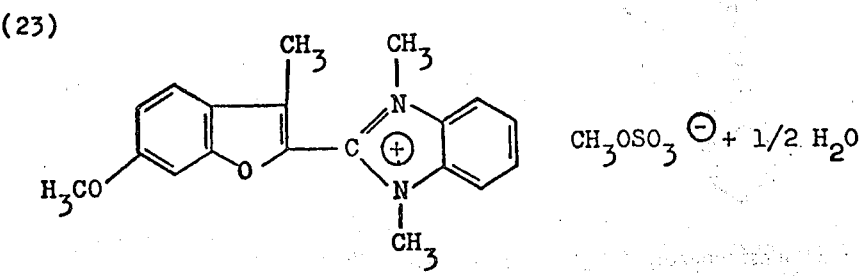
Melting point: 182°–183°C (24)

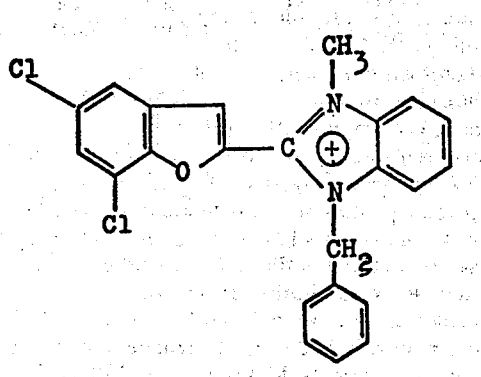
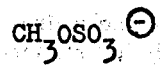

Melting point: 187°–189°C
are obtained. These products possess similar properties to the compound manufactured above and are suitable for whitening synthetic fibres, especially of polyacrylonitrile.

the substituted 6-methoxy-2-[1-benzyl-benzimidazolyl-(2)]-benzofuranes used for the manufacture of the compounds of the formulae (20), (21) and (22) can be manufactured as follows:

42.6 g of 6-methoxycoumarilic acid chloride are introduced at room temperature into a solution of 32.0 g of 2-nitro-4-methyl-aniline in 400 ml of pyridine, in the course of which the temperature of the reaction mixture rises to about 40°C and a yellow crystalline precipitate is formed. After 1 hour, the reaction mixture is warmed to 80 - 85°C, whereby a solution is produced which is stirred for 1 hour at this temperature and thereafter allowed to cool. The crystalline yellow precipitate is filtered off, washed with cold alcohol and dried. Yield: 45.2 g of 6-methoxy-coumarilic acid 4-methyl-2-nitroanilide. Melting point: 191° to 192°C.

To reduce the nitro compound, 42 g of iron filings are surface-etched with 42 ml of water and 8.3 ml of 80% strength acetic acid for 30 minutes at 90°C. Thereafter, 111 ml of cyclohexanone are added, the mixture is warmed to 95° - 100°C and 45.2 g of nitro compound are introduced in small portions over the course of 1 hour. The reaction mixture is boiled for 4 hours under reflux, then rendered weakly alkaline by careful addition of about 8.3 g of sodium carbonate, treated with 200 ml of cyclohexanone and again brought to the boil; the iron sludge is then filtered off hot and the filter residue is washed with hot alcohol. The filtrate is thereafter steamdistilled and the solid residue is filtered off, washed with water and subsequently dried. The yield of crude 6-methoxycoumarilic acid 4-methoxy-2-aminoanilide is 39.4 g. Melting point: 178° to 181°C.

To manufacture the benzimidazole compound, 39.4 g of the o-amino-acylamino compound manfactured above are stirred with 485 ml of ethylene glycol monomethyl ether, 40.2 g of 37.2% strength hydrochloric acid are added and the reaction mixture is warmed for 4 hours to 100° - 104°C under reflux and is subsequently poured into 4.800 ml of cold water, containing 47 ml of 30% strength sodium hydroxide solution. The initially oil benzimidazole crystallises after standing for several hours and is then filtered off, washed with water and dried. After twice recrystallising from toluene using fuller's earth as an auxiliary, 26.4 g of 6-methoxy-2-[5-methyl-benzimidazolyl-(2)]-benzofurane are obtained. Melting point: 214° to 215°C.

26.4 g of the benzimidazole obtained above are introduced into 200 ml of methyl ethyl ketone whilst stirring. After adding 13.12 g of anhydrous potassium carbonate, 0.95 g of potassium iodide and 12.35 g of benzyl chloride the reaction mixture is boiled for 12 hours under reflux, inorganic salts are then filtered off and washed with methyl ethyl ketone, the filtrate is concentrated and the product which crystallises out after cooling is filtered off and dried. Two recrystallisations from toluene using fuller's earth as an auxiliary yield 15.3 g of 6-methoxy-2-[1-benzyl-5-methyl-benzimidazolyl(2)-benzofurane. Melting point: 157° to 159°C.

If instead of 2-nitro-4-methylaniline the equivalent amount of 2-nitro-4-chloroaniline or 2-nitro-4-methylsulphonylaniline is used and in other respects the procedure described above is followed, 6-methoxy-2-[1-benzyl-5-chlorobenzimidazolyl(2)]-benzofurane of melting point 143.5° to 144.5°C, or 6-methoxy-2-[1-benzyl-5-methylsulphonyl-benzimidazolyl-(2)]benzofurane of melting point 166° to 169°C, are respectively obtained.

EXAMPLE 7

To manufacture the quaternary compound of the formula (25)

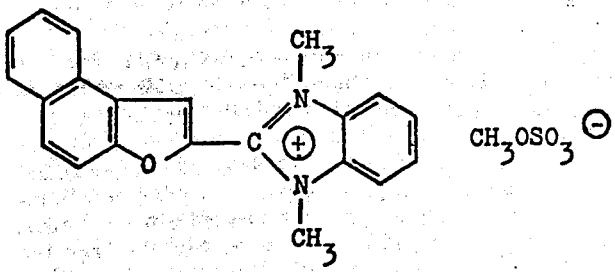

5.96 g of 2-[1-methyl-benzimidazolyl-(2)]-4,5-benzocoumarone are dissolved in 120 ml of dioxane by warming to 90° - 95°C. 3.15 g of dimethyl sulphate are then added dropwise whilst stirring, whereupon the quaternary salt precipitates after a short time. After stirring for a further hour at 90° to 95°C the mixture is allowed to cool to 40°C and the product is filtered off, washed with dioxane and dried in vacuo at 50° to 60°C. Redissolving and reprecipitating from isopropanol, and subsequent crystallisation from ethanol, yields the quaternary compound as light beige crystals of melting point 202° to 204°C.

The compound dissolves in water to give a blue fluorescence in daylight and is outstandingly suitable for brightening organic materials, especially polyacrylonitrile fibres.

The 2-[-1-methyl-benzimidazolyl-(2)]-4,5-benzocoumarone used above is obtained as follows:

42.5 g of 4,5-benzocoumarine-2-carboxylic acid are boiled with 95 ml of thionyl chloride under reflux until a clear solution has been produced. Thereafter the excess thionyl chloride is distilled off in vacuo, whereupon the carboxylic acid chloride is obtained as a light beige-brown crystalline residue, in almost quantitative yield. Crude melting point: 116° to 116.5°C.

44.9 g of the carboxylic acid chloride manufactured above, in a finely powdered form, are introduced into a solution of 31.9 g of N-methyl-o-nitroaniline in 400 ml of pyridine at room temperature, whilst stirring, in the course of which the internal temperature rises slightly. After 15 minutes, the reaction mixture is warmed to 80° - 85°C, kept for 1 hour at this temperature and then poured, whilst still hot, into 3,500 to 4,000 ml of cold water, whereupon the acylation product first separates out as an oil which crystallises after some time. After it has solidified, the product is filtered off, washed with water and dried in vacuo at 40° to 50°C. The yield of crude 4,5-benzocoumarine-2-carboxylic acid N-methyl-o-nitroanilide is 57.5 g. Melting point: 136° to 138°C.

To manufacture the o-amino-acylamino compound, 49.8 g of iron filings in 51 ml of water are surface-etched with 10 ml of 80% strength acetic acid at 90°C for 30 minutes. Thereafter 133 ml of cyclohexanone are added, the mixture is warmed to 95° - 100°C and 57.5 g of 4,5-benzocoumarine-2-carboxylic acid N-methyl-o-nitroanilide are introduced over the course of 45 minutes, in small portions. The reaction mixture is boiled for 4 hours under reflux and after addition of 51 ml of water is rendered alkaline with about 10 g of sodium carbonate, 250 ml of cyclohexanone are added and after reaching the boiling point the mixture is filtered hot and the filter residue is washed with hot ethanol. Thereafter the filtrate is steam-distilled and the solid residue is filtered off, washed with water and then dried. The yield of crude 4,5-benzocoumarine-2-carboxylic acid N-methyl-2-aminoanilide is 46.2 g. Melting point: 196° to 198°C.

To manufacture the benzimidazole compound, 46.2 g of the o-amino-acylamino compound manufactured above are suspended in 440 ml of ethylene glycol monomethyl ether, 35.3 g of 37.2% strength hydrochloric acid are added and the mixture is heated to 100° - 105°C under reflux for 4 hours, whilst stirring, whereby a fine suspension of the benzimidazole hydrochloride is produced. After addition of 500 ml of ethylene glycol monomethyl ether the reaction mixture is rendered weakly alkaline to phenolphthalein at 90° to 95°C by means of about 40 ml of 30% strength sodium hydroxide solution and is thereafter poured into 4,000 ml of cold water whilst stirring, and the product which has precipitated is filtered off, washed with water and dried. Recrystallisation from ethanol with the aid of decolourising charcoal yields 32.6 g of 2-[1-methyl-benzimidazolyl]-(2)]-4,5-benzocoumarine in almost colourless crystals. Melting point: 208° to 209°C.

EXAMPLE 8

To manufacture the quaternary compound of the formula

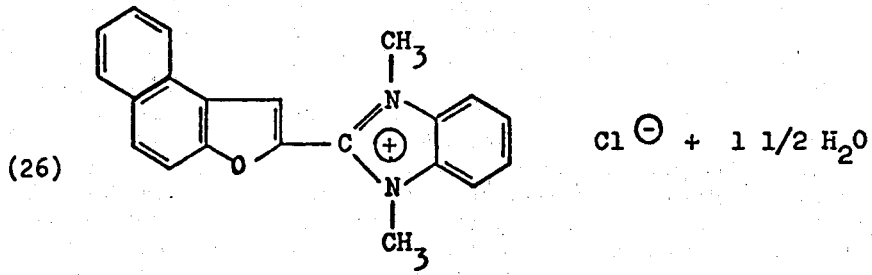

6.0 g of 2-[1-methyl-benzimidazolyl-(2)]-4,5-benzocoumarone, the manufacture of which is described in Example 7, are stirred with 150 ml of dioxane and 16 g of methyl iodide for 24 hours in a water bath at 55° to 60°C bath temperature. The precipitate formed is filtered off whilst still warm, washed with dioxane and dried. Yield: 7.5 g. A sample recrystallised from ethanol forms light yellow crystals of melting point 262° to 265°C.

For conversion into the corresponding methochloride compound, 7.5 g of the quaternary methoiodide manufactured above are suspended in 500 ml of 90% strength ethanol and the suspension is warmed to 45° - 50°C. An alcoholic suspension of freshly manufactured silver chloride, which has been prepared from 10.0 g of silver nitrate in the usual manner, is then added and the reaction mixture is stirred for 5 hours at 45° to 50°C. The silver halide is then filtered off and washed with warm 50% strength ethanol, the filtrate is clarified with decolourising charcoal and the aqueous-alcoholic solution is then evaporated to dryness in vacuo. After crystallisation of the evaporation residue from water containing a little hydrochloric acid, the compound is obtained as light yellow fine small crystal needles. Melting point: 254° to 256°C. (Decomposition).

The compound dissolves in water to give a strong blue fluorescence in daylight and is outstandingly suitable for brightening organic materials, especially of polyacrylonitrile fibres.

If instead of 2-[1-methyl-benzimidazolyl-(2)]-4,5-benzocoumarine the equivalent amount of 6-methoxy-2-[1-benzyl-5-methylsulphonyl-benzimidazolyl-(2)]-benzofurane is used and in other respects the procedure described in the example is followed, the quaternary compound of the formula

(27) 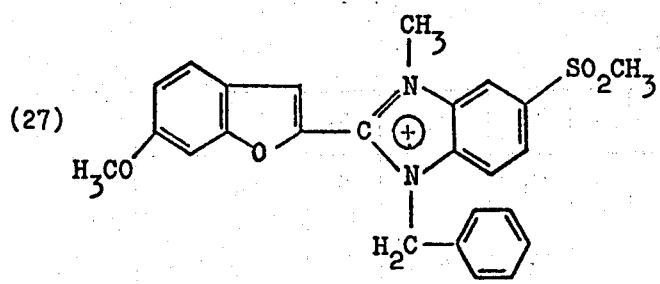   $Cl^{\ominus} + 1\ 1/2\ H_2O$ is obtained, after recrystallisation from water and drying in vacuo at 60° to 65°C, in the form of pale greenish-tinged yellow crystals. Melting point: 148° to 150°C.

This product possesses similar properties to the compound described above.

EXAMPLE 9

The compound of the formula

(28) 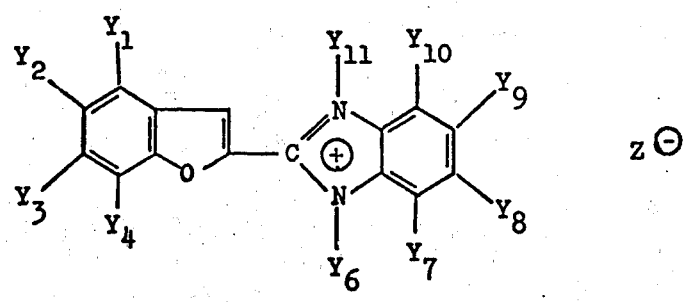   $z^{\ominus}$ listed in Table I are obtained in an analogous manner to that described in Examples 1 to 8.

TABLE I

| Compound | $Y_1$ | $Y_2$ | $Y_3$ | $Y_4$ | $Y_5$ | $Y_6$ | $Y_7$ | $Y_8$ | $Y_9$ | $Y_{10}$ | $Y_{11}$ | z |
|---|---|---|---|---|---|---|---|---|---|---|---|---|
| 29 | $CH_3$ | H | H | H | H | –⟨⟩–Cl | H | H | Cl | H | $-CH_2CHOH$ | Cl |
| 30 | H | $C_2H_5$ | H | H | H | $C_2H_5$ | H | H | $-C(CH_3)_3$ | H | $CH_3$ | $CH_3OSO_3$ |
| 31 | H | H | H | H | –⟨⟩–$OCH_3$ | $CH_3$ | H | H | H | H | $-CH_2COOCH_3$ | Br |
| 32 | $CH_3$ | H | $CH_3$ | H | $C_2H_5$ | $CH_3$ | H | H | $-SO_2C_2H_5$ | H | $-CH_2$–⟨⟩ | Cl |
| 33 | H | H | Cl | H | H | $CH_3$ | H | $CH_3$ | $-OCH_3$ | H | $-CH_2$–⟨⟩–$OCH_3$ | Cl |
| 34 | H | H | $OCH_3$ | H | $CH_3$ | piperidino | H | H | H | H | $-C_2H_5$ | $C_2H_5OSO_3$ |
| 35 | H | H | $OCH_3$ | Br | $CH_3$ | –⟨⟩–$CH_3$ | H | H | H | H | $CH_3$ | $CH_3$–⟨⟩–SC |

TABLE I —Continued

| Compound | $Y_1$ | $Y_2$ | $Y_3$ | $Y_4$ | $Y_5$ | $Y_6$ | $Y_7$ | $Y_8$ | $Y_9$ | $Y_{10}$ | $Y_{11}$ | Z |
|---|---|---|---|---|---|---|---|---|---|---|---|---|
| 36 | $OCH_3$ | H | H | H | H | $-CH_2-\langle \rangle$ | H | $CH_3$ | H | Cl | $CH_3$ | $CH_3OSO_3$ |
| 37 | $OCH_3$ | Br | H | Br | $CH_3$ | $CH_3$ | H | H | H | H | $C_2H_5$ | $C_2H_5OSO_3$ |
| 38 | H | Cl | $OCH_3$ | H | H | $CH_3$ | $CH_3$ | $CH_3$ | H | H | $-CH_2-\langle \rangle -Cl$ | Cl |
| 39 | $OCH_3$ |  | $OCH_3$ | $CH_3$ | H | $-\langle \rangle$ | H | H | H | H | $CH_3$ | $\langle \rangle -SO_3$ |
| 40 | H | $OCH_3$ | $OCH_3$ | H | $-\langle \rangle$ | $CH_3$ | H | H | H | H | $CH_2CN$ | Cl |
| 41 | $OCH_3$ | H | $OCH_3$ | Cl | $CH_3$ | $-CH_2-\langle \rangle$ | H | H | H | H | $CH_3$ | $CH_3-\langle \rangle -SO_3$ |
| 42 | H | $OCH_3$ | $OCH_3$ | $OCH_3$ | $-\langle \rangle$ | $CH_3$ | H | $CH_3$ | Cl | H | $C_2H_5$ | $C_2H_5OSO_3$ |
| 43 | $OCH_3$ | $OCH_3$ | $OCH_3$ | $OCH_3$ | $OCH_3$ | $CH_3$ | H | H | H | H | $CH_3$ | $CH_3OSO_3$ |
| 44 | $C_2H_5$ | H | H | $OCH_3$ | H | $-CH_2-\langle \rangle$ | H | H | H | H | $-CH_2CONH_2$ | Cl |
| 45 | H | H | $OCH_3$ | H | $-\langle \rangle -OCH_3$ | $CH_3$ | H | H | H | H | $CH_3$ | $CH_3OSO_3$ |
| 46 | H | $CH_3$ | H | H | $-\langle \rangle (CH_3, OCH_3)$ | $-CH_2CH_2CH_3$ | H | H | H | H | $CH_3$ | $CH_3OSO_3$ |
| 47 | $CH_3$ | H | $CH_3$ | H | $-CH(CH_3)_2$ | $CH_3$ | H | H | H | H | $-CH_2-\langle \rangle -Cl$ | Cl |
| 48 | $CH_3$ | Br | $OCH_3$ | H | H | $CH_3$ | H | Cl | Cl | H | $CH_3$ | $-CH_3-\langle \rangle -SO_3$ |
| 49 | H | $C_2H_5$ | $OCH_3$ | H | H | $-\langle \rangle -Cl$ | H | H | Cl | H | $CH_3$ | $CH_3OSO_3$ |
| 50 | H | H | $OC_4H_9$ | H | $CH_3$ | $-CH_2CH_2CN$ | H | H | H | H | $CH_3$ | $CH_3OSO_3$ |
| 51 | H | H | $OCH_3$ | H | $-\langle \rangle$ | $-\langle \rangle$ | H | H | $OCH_3$ | H | $-CH_2-\langle \rangle$ | Cl |
| 52 | $OCH_3$ | H | $CH-CH / CH \backslash CH$ |  | H | $CH_3$ | H | H | H | H | $CH_3$ | $CH_3OSO_3$ |
| 53 | $CH-CH / CH \backslash CH$ |  | H | H | H | $CH_3$ | H | Br | H | $CH_3$ | $CH_3$ | $CH_3OSO_3$ |
| 54 | H | $CH-CH / CH \backslash CH$ |  | H | H | $C_2H_5$ | H | H | H | H | $C_2H_5$ | $C_2H_5OSO_3$ |

EXAMPLE 10

0.12 ml of 85% strength formic acid are added to 100 ml of water. A solution of the optical brightener of the formula (8) is prepared by dissolving 1 g in 1,000 ml of water. 1.5 ml of this stock solution are added to the solution described above. The liquor thus obtained is warmed to 60°C and a polyacrylonitrile fabric weighing 3 g is introduced into it. The temperature is raised to 95°–98°C over the course of 10 to 15 minutes and the mixture is left at this temperature for one hour. The fabric is then rinsed for 2 minutes in running cold water and is subsequently dried for 20 minutes at 60°C. The fabric thus treated shows a white brilliant appearance.

If the procedure indicated in the above example is followed but instead of the brightener mentioned therein the compounds of the formula (9), (10), (12), (13), (15), (17), (20), (22), (23), (25), (26) or (27) are used, similar results are obtained.

EXAMPLE 11

0.2 g of sodium nitrate, 0.2 g of 80% strength sodium chlorite, 0.2 g of oxalic acid or an equivalent amount of another organic or inorganic acid suitable for this purpose are added to 100 ml of water. A solution of the brightener of the formula (10) is prepared by dissolving 1 g of the said brightener in 1,000 ml of water. 1.5 ml of this stock solution are added to the solution described above. This liquor is warmed to 60°C, a polyacrylonitrile fabric weighing 3 g is then added, the temperature is raised to 95°–98°C over the course of 10 to 15 minutes and the bath is left for 60 minutes at this temperature. The fabric is then rinsed in cold water and dried for 20 minutes at 60°C. The fabric thus treated shows a white, brilliant appearance.

Similar results are obtained if the same procedure as described above is followed but the brighteners of the formulae (8), (9), (12), (13), (15), (18), (20), (21), (22), (25), (26) or (27) are employed.

EXAMPLE 12

0.1 g of oxalic acid, 0.1 g of sodium acetate, 0.0125 g of sodium bisulphite amd 0.025 g of a polyphosphate, as a complex-forming agent, are added to 100 ml of water. A solution of the optical brightener of the formula (10) is prepared by dissolving 1 g in 1,000 ml of water. 6 ml of this stock solution are added to the solution described above. The aqueous liquor containing the brightener is warmed to 60°C and a hank of polyacrylonitrile ("(Courtelle," Courtaulds, London, England) weighing 3 g is introduced into the liquor. The temperature is raised to 98°C over the course of 10 to 15 minutes and the material is treated for 30 minutes at this temperature. Thereafter it is rinsed with cold water and dried. The fibre material thus treated shows an attractive, white appearance.

If instead of the brightener described above a brightener of the formula (9), (11), (13), (15), (20), (21), (22), (23), (25) or (26) is used and in other respects the procedure indicated in the example is followed, similar effects are produced on the fibre material mentioned.

EXAMPLE 13

1 g of the optical brightener of the formula (8) is dissolved in 1,000 ml of water. 3 ml of this stock solution are added to 100 ml of water, the liquor containing the brightener is warmed to 60°C, and a nylon fabric weighing 3 g is then added. The temperature is raised to 92°–95°C over the course of 10 to 15 minutes and the fabric is left at this temperature for 30 minutes. After rinising and drying, the material treated in this way shows an attractive, white appearance.

Similar results are achieved with the brighteners of the formulae (9), (10), (12), (13), (20), (21) or (22).

EXAMPLE 14

0.2 g of sodium chlorite (80% strength), 0.2 g of sodium nitrate and 0.2 g of oxalic acid or an equivalent amount of another organic or inorganic acid suitable for this purpose are added to 100 ml of water. A solution of the optical brightener of the formula (9) is prepared by dissolving 1 g in 1,000 ml of water. 3 ml of this stock solution are added to the solution described above. This aqueous liquor containing the brightener is warmed to 60°C. A nylon fabric weighing 3 g is then added. The temperature is raised to 85°C over the course of 10 to 15 minutes and the system is left at this temperature for 30 minutes. The temperature is then raised to 95°–98°C over the course of 10 to 15 minutes and the system is again left at this temperature for 30 minutes. The fabric is then rinsed for 2 minutes in running cold water and is subsequently dried for 20 minutes at 60°C. The material thus treated shows an attractive, white appearance.

EXAMPLE 15

1 g of the optical brightener of the formula (9) is dissolved in 1,000 ml of water. A polyester fabric is padded with this solution at 20°C (expression effect 50 to 60%, roller pressure 30 kg/cm², speed 3m/minute). The fabric is dried for 20 minutes at 60°C and subsequently set for 30 seconds at 200°C. The fabric treated in this way shows a white, brilliant appearance.

A similar result is achieved if the brightener of the formula (8), (10), (12), (19), (20), (21) or (22) is employed and in other respects the procedure described above is followed.

EXAMPLE 16

0.06 ml of 80% strength acetic acid is added to 95 ml of water. A solution of the optical brightener of the formula (9) is manufactured by dissolving 1 g in 1,000 ml of water. 6 ml of this stock solution are added to the solution described above. The liquor containing the brightener is warmed to 40°C and an acetate fabric weighing 3 g is then added thereto. The temperature is raised to 75°–80°C over the course of 10 to 15 minutes and the liquor is left at this temperature for 30 minutes. The fabric is then rinsed in running water and dried. The fabric treated in this way shows a white, brilliant appearance.

Similar results are obtained with the brighteners of the formulae (8), (10), (12), (13), (14), (15), (17), (19), (20), (22), (23) or (25).

EXAMPLE 17

80 g of a degraded starch (for example NERODUX 100$^R$ of Messrs. Blattmann & Co. Wadenswil, Switzerland) are dissolved in 1,000 ml of water, heated to 90°C, over the course of 15 minutes to give a colloidal solution, and this is mixed with a solution, prepared hot, of 5 g of the optical brightener of the formula (10) in 50 ml of distilled water. The resulting mixture containing starch and optical brightener has a pH value of 5.5 to 6.0.

A sized printing paper is surface-coated with this coating liquor in a sizing press and the coated paper is dried at about 50° to 120°C in the drying part of the paper machine. A paper of substantially improved degree of whiteness is thus obtained.

Instead of using sized paper, sized cardboard can be used with equal success.

EXAMPLE 18

10 parts of cotton cretonne are treated, at a temperature of 40°C, in 300 parts of a liquor containing 0.6 part of a cationic agent of the type of bis-stearyl-bis-methylammonium chloride, which improved the handle of the textile material, and 0.01 part of the brightener of the formula (10), for 15 minutes. After drying, the treated fabric shows an attractive white effect and additionally a soft handle.

A considerably stronger white shade is obtained if, in the above example 0.06 part of the brightener mentioned is used instead of 0.01 part.

I claim:
1. A benzofurane of the formula

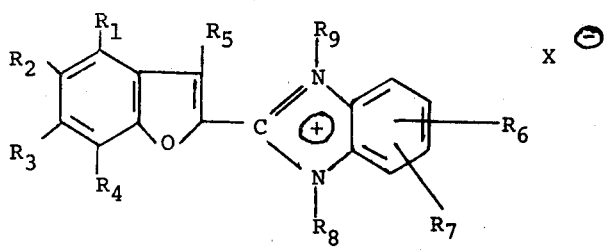

wherein
- $R_1$ denotes hydrogen or a lower alkyl group or together with $R_2$ denotes a fused benzene radical,
- $R_2$ denotes hydrogen, a lower alkyl or alkoxy group, chlorine, bromine, carboxyl, aminocarbonyl, sulphonic acid, aminosulphonyl, or together with $R_3$ denotes a fused benzene radical,
- $R_3$ denotes hydrogen, lower alkyl, alkoxy or together with $R_4$ denotes a fused benzene radical,
- $R_4$ denotes hydrogen, a lower alkyl group, chlorine or bromine,
- $R_5$ denotes hydrogen, a lower alkyl group or phenyl,
- $R_6$ denotes hydrogen, lower alkyl, lower alkoxy, chlorine, bromine, or phenyl,
- $R_7$ is hydrogen,
- $R_8$ denotes a lower alkyl group, a hydroxy-lower-alkyl group, cyanoethyl, phenyl which is unsubstituted or substituted by a chlorine, bromine, a lower alkyl or lower alkoxy group, or phenyl loweralkyl,
- $R_9$ denotes a lower alkyl group, a hydroxy-lower-alkyl group, phenyl lower-alkyl which is unsubstituted or substituted by chlorine or lower alkoxy, or the $-CH_2CN$, $-CH_2CONH_2$ or $-CH_2-COOR$ radical, wherein R represents alkyl with one to four carbon atoms, and
- X denotes halogen, lower alkylsulphonic acid or phenylsulphonic acid which is unsubstituted or substituted by lower alkyl.

2. A benzofurane of claim 1, wherein
- $R_1$ denotes hydrogen, methyl, ethyl, methoxy, chlorine, or bromine, or together with $R_2$ denotes a fused benzene radical,
- $R_2$ denotes hydrogen, methyl, ethyl, methoxy, chlorine, or bromine, or together with $R_3$ denotes a fused benzene radical,
- $R_3$ denotes hydrogen, methyl, ethyl, alkoxy with one to four carbon atoms, chlorine, bromine, or together with $R_4$ denotes a fused benzene radical,
- $R_4$ denotes hydrogen, alkyl with one to four carbon atoms, methoxy, chlorine, or bromine,
- $R_5$ denotes hydrogen, alkyl with one to four carbon atoms, or phenyl which is unsubstituted or substituted by methyl and/or methoxy,
- $R_6$ denotes hydrogen, alkyl with one to four carbon atoms, alkylsulphonyl with one to four carbon atoms, methoxy, or bromine,
- $R_7$ denotes hydrogen, methyl, methoxy, chlorine, or bromine,
- $R_8$ denotes alkyl with one to four carbon atoms, hydroxyalkyl with two to four carbon atoms, cyanoethyl, phenyl which is unsubstituted or substituted by chlorine, methyl or methoxy, cyclohexyl, or benzyl,
- $R_9$ denotes alkyl with one to four carbon atoms which is unsubstituted or substituted by hydroxyl or alkoxy with one to four carbon atoms, benzyl which is unsubstituted or substituted by chlorine or methoxy, or a radical $-CH_2CN$, $-CH_2CONH_2$ or $-CH_2COOR$, wherein
- R represents an alkyl group with one to four carbon atoms, and
- X denotes halogen, an alkylsulphonic acid radical with one to four carbon atoms, or a phenylsulphonic acid radical which is unsubstituted or substituted by methyl.

3. A benzofurane of claim 1, wherein
- $R_1$ denotes hydrogen or together with $R_2$ denotes a fused benzene radical,
- $R_2$ denotes hydrogen, chlorine, or bromine,
- $R_3$ denotes hydrogen, alkyl group with one to four carbon atoms, an alkoxy group with one to four carbon atoms,
- $R_4$ denotes hydrogen, chlorine, or bromine,
- $R_5$ denotes hydrogen or an alkyl group with one to four carbon atoms,
- $R_6$ and $R_7$ are hydrogen,
- $R_8$ denotes an alkyl group with one to four carbon atoms,
- $R_9$ denotes an alkyl group with one to four carbon atoms, a hydroxyalkyl group with one to four carbon atoms, or benzyl, and
- X denotes halogen, a lower alkyl-sulphonic acid radical or a methylphenylsulphonic acid radical.

4. A benzofurane of claim 1 wherein
- $R_1$ and $R_2$ denote hydrogen or together denote a fused benzene radical,
- $R_3$ denotes hydrogen, methoxy or methyl,
- $R_4$ is hydrogen,
- $R_5$ denotes hydrogen or methyl,
- $R_6$ is in the 5-position and denotes hydrogen, methyl, methoxy, chlorine or methylsulphonyl,
- $R_7$ is hydrogen,
- $R_8$ denotes methyl, phenyl or benzyl,
- $R_9$ denotes methyl or benzyl, and
- X denotes chlorine, the methylsulphonic acid radical or the p-toluenesulphonic acid radical.

5. A benzofurane of the formula

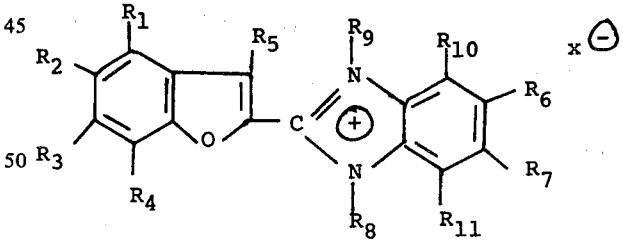

wherein
- $R_1$ is hydrogen or taken together with $R_2$ is a fused benzene radical,
- $R_2$ is hydrogen, or chlorine,
- $R_3$ is methyl or lower alkoxy,
- $R_4$ is hydrogen or chlorine,
- $R_5$ is hydrogen or methyl,
- $R_6$ is hydrogen, methyl, chlorine, or methylsulphonyl,
- $R_7$, $R_{10}$, and $R_{11}$ are hydrogen,
- $R_8$ is methyl, phenyl, benzyl, or cyclohexyl, and
- $R_9$ is methyl or benzyl.

* * * * *